(12) United States Patent
Palepu

(10) Patent No.: US 9,616,098 B2
(45) Date of Patent: Apr. 11, 2017

(54) FORMULATIONS OF VANCOMYCIN

(71) Applicant: SCIDOSE, LLC, Amherst, MA (US)

(72) Inventor: Nagesh R. Palepu, Southampton, PA (US)

(73) Assignee: SciDose, LLC, Amherst, MA (US)

(*) Notice: Subject to any disclaimer, the term of this patent is extended or adjusted under 35 U.S.C. 154(b) by 0 days.

(21) Appl. No.: 14/894,215

(22) PCT Filed: May 30, 2014

(86) PCT No.: PCT/US2014/040396
§ 371 (c)(1),
(2) Date: Nov. 25, 2015

(87) PCT Pub. No.: WO2014/194296
PCT Pub. Date: Dec. 4, 2014

(65) Prior Publication Data
US 2016/0101147 A1   Apr. 14, 2016

Related U.S. Application Data

(60) Provisional application No. 61/828,739, filed on May 30, 2013.

(51) Int. Cl.
| | | |
|---|---|---|
| A61K 38/12 | (2006.01) | |
| A61K 38/14 | (2006.01) | |
| A61K 47/02 | (2006.01) | |
| A61K 47/10 | (2006.01) | |
| A61K 47/12 | (2006.01) | |
| A61K 9/08 | (2006.01) | |
| A61K 9/00 | (2006.01) | |

(52) U.S. Cl.
CPC ............ *A61K 38/12* (2013.01); *A61K 9/0019* (2013.01); *A61K 9/08* (2013.01); *A61K 38/14* (2013.01); *A61K 47/02* (2013.01); *A61K 47/10* (2013.01); *A61K 47/12* (2013.01)

(58) Field of Classification Search
CPC ........ A61K 38/12; A61K 38/14; A61K 47/02; A61K 47/10; A61K 47/12; A61K 9/0019; A61K 9/08
See application file for complete search history.

(56) References Cited

U.S. PATENT DOCUMENTS

| | | |
|---|---|---|
| 4,885,275 A | 12/1989 | Robinson |
| 7,364,874 B2 | 4/2008 | Totsuka et al. |
| 2003/0229047 A1* | 12/2003 | Joshi-Hangal ....... A61K 9/0019 514/49 |

FOREIGN PATENT DOCUMENTS

| | | |
|---|---|---|
| JP | 2008201778 A | 9/2008 |
| WO | 2012054447 A2 | 4/2012 |

OTHER PUBLICATIONS

English translation of JP2008201778 specificaiton 31 pages; Sep. 4, 2008.*
Vancomycin Drug Label ([online] retrieved on Aug. 4, 2016 from: https://dailymed.nlm.nih.gov/dailymed/archives/fdaDrugInfo.cfm?archiveid=1651; 2006; 12 pages).*
International Search Report based on International Application No. PCT/US2014/040396 mailed Oct. 15, 2014. (3 pages).

* cited by examiner

*Primary Examiner* — Ernst V Arnold
(74) *Attorney, Agent, or Firm* — Lucas & Mercanti, LLP

(57) ABSTRACT

Vancomycin-containing compositions substantially free of precipitation after at least about 12 months of storage at refrigerated or ambient conditions are disclosed. The compositions include vancomycin or a pharmaceutically acceptable salt thereof; a polar solvent including propylene glycol, polyethylene glycol and mixtures thereof; lactic acid, a lactate salt, or mixtures thereof; and optionally, a pH adjuster in an amount sufficient to maintain a pH of the compositions at from about 3 to about 8.

19 Claims, No Drawings

FORMULATIONS OF VANCOMYCIN

CROSS-REFERENCE TO RELATED APPLICATIONS

This application is a U.S. national stage of PCT/US2014/040396 filed on May 30, 2014 which claims the benefit of priority from U.S. Patent Application No. 61/828,739 filed May 30, 2013, the contents of each of which are incorporated herein by reference.

BACKGROUND OF THE INVENTION

Vancomycin is a glycopeptide antibiotic represented by the following structural formula (I):

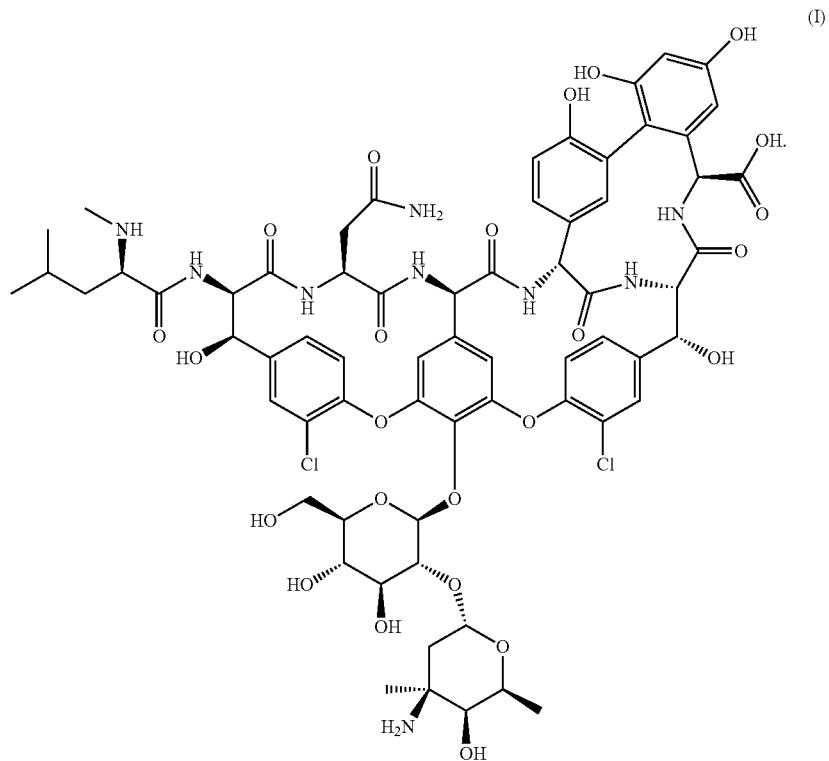 [SMILES: CN[C@H](CC(C)C)C(=O)N[C@H]1C(=O)N[C@@H](CC(N)=O)C(=O)N[C@H]2C(=O)N[C@H]3C(=O)N[C@H](C(=O)N[C@H](C(=O)O)c4cc(O)cc(O)c4-c4cc3ccc4O)[C@H](O)c3ccc(c(Cl)c3)Oc3cc2cc(c3O[C@@H]2O[C@H](CO)[C@@H](O)[C@H](O)[C@H]2O[C@H]2C[C@](C)(N)[C@H](O)[C@H](C)O2)Oc2ccc(cc2Cl)[C@H]1O]

Vancomycin is used in the prophylaxis and treatment of infections caused by Gram-positive bacteria. Vancomycin is used in the treatment of methicillin-resistant *Staphylococcus aureus* (MRSA) and Methicillin-susceptible *Staphylococcus aureus* (MSSA), and to treat patients who are penicillin-resistant. Vancomycin HCl is commercially available inter alia, as a frozen premixed formulation, which can be used for intravenous administration after thawing.

Vancomycin exhibits premature degradation after reconstitution of the lyophilized product. Vancomycin is stable in water for approximately 24 hours after reconstitution, and is therefore, not suitable for long-term storage in liquid form. There is a need for vancomycin formulations with increased stability. The present invention addresses this need.

SUMMARY OF THE INVENTION

In some aspects of the invention, the liquid vancomycin-containing compositions include a) vancomycin or a pharmaceutically acceptable salt thereof; b) a polar solvent comprising propylene glycol, polyethylene glycol, or mixtures thereof; c) lactic acid, a lactate salt or mixtures thereof; and optionally d) a pH adjustor, in an amount sufficient to maintain a pH of the vancomycin-containing composition at from about 3 to about 8.

In some aspects of the invention, the amount of vancomycin included in the compositions, as calculated on the basis of the HCl salt, is from about 25 mg/mL to about 150 mg/mL. In other aspects of the invention, the amount of vancomycin as calculated on the basis of the HCl salt included in the compositions is from about 2.5 mg/mL to about 15 mg/mL.

In some aspects of the invention, the compositions include from about 25% (v/v) to about 100% (v/v) of a polar solvent, more preferably from about 25% (v/v) to about 50% (v/v). In other aspects of the invention, the compositions include from about 1.20% (v/v) to about 5% (v/v) of a polar solvent.

Still further aspects of the invention include methods of treatment using vancomycin-containing compositions and kits including the same.

One of the advantages of the liquid compositions prepared according to the current invention is that they have substantially improved long-term stability. The inventive vancomycin-containing compositions are substantially free of precipitation after at least about 24 months of storage at a temperature of from about 5° C. to about 25° C. The inventive vancomycin-containing compositions also exhibit less than about 6% degradation of vancomycin B, as determined by high performance liquid chromatography ("HPLC") at a wavelength of 280 nm, after at least about 18 months of storage at a temperature of from about 5° C. to about 25° C. As used herein, the vancomycin concentration is measured using the United States Pharmacopeia (USP) official monograph for vancomycin for injection described in USP 36, the contents of which are incorporated by reference herein.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

As used herein, "relative retention time" ("RRT") is calculated by dividing the retention time of the peak of interest by the retention time of the main peak. Any peak with an RRT<1 elutes before the main peak, and any peak with an RRT>1 elutes after the main peak.

For purposes of the present invention, "substantially free of precipitation" shall be understood to include vancomycin-containing compositions in which precipitation is not visually observed after a period of at least about 12 months at a temperature of from about 5° C. to about 25° C. "Substantially free of total impurities" shall be understood to include vancomycin-containing compositions which exhibit less than about 6% degradation of vancomycin B, as determined by HPLC at a wavelength of 280 nm, after at least about 12 months of storage at a temperature of from about 5° C. to about 25° C. The amount of impurities is further calculated as being based upon the original amount vancomycin B (or salt thereof) being present in the composition or formulation. In accordance with the USP official monograph for vancomycin, the concentration of vancomycin is determined by measuring the amount of vancomycin B by HPLC at a wavelength of 280 nm. For the detailed procedure used to calculate vancomycin B, refer to the USP monograph for vancomycin. In some examples, a normalized loss of vancomycin B may be calculated by dividing the concentration of vancomycin B at the testing point by the initial concentration of vancomycin B, and then multiplying by 100.

For purposes of the present invention, a "pharmaceutically acceptable fluid" is a fluid which is suitable for pharmaceutical use, for example but not limited to solvents, vehicles, large volume parenterals (LVPs) such as normal saline (i.e., 0.9% sodium chloride) or 5% dextrose in water ("$D_5W$"), and/or additional diluents, if desired, etc.

In accordance with one aspect of the invention, there are provided vancomycin-containing compositions including:
a) about 25 mg/mL to about 150 mg/mL vancomycin or a pharmaceutically acceptable salt thereof; and
b) a pharmaceutically acceptable fluid having a pH of about 3 to about 8, comprising:
  i) about 25% (v/v) to about 50% (v/v) of a polar solvent comprising propylene glycol, polyethylene glycol, or mixtures thereof;
  ii) about 0.25 mmole to about 0.94 mmole of lactic acid, lactate or mixtures thereof per ml of pharmaceutically acceptable fluid, which can be prepared, for example, by using about 50% (v/v) to about 75% (v/v) of a solution comprising 0.5M to 1.25M lactate. In terms of mass amount, this may include, for example, about 22% (w/v) to about 85% (w/v) lactic acid per se, or a similar lactate concentration adjusted appropriately when using a lactate salt or mixtures thereof); and
  iii) optionally, a pH adjustor in an amount sufficient to maintain a pH of the vancomycin-containing composition at from about 3 to about 8.

The inventive compositions are substantially free of visible precipitation after at least about 12 months of storage at a temperature of from about 5° C. to about 25° C. Preferably, the vancomycin-containing compositions are substantially free of precipitation for at least 24 months. The total impurities in the inventive compositions resulting from the degradation of vancomycin in the compositions is less than about 6% degradation of vancomycin B, as determined by HPLC at a wavelength of 280 nm, after at least about 12 months of storage at a temperature of from about 5° C. to about 25° C. Preferably, the vancomycin-containing compositions are stable for at least 24 months of storage at a temperature of from about 5° C. to about 25° C. Without being bound by theory, it is believed that the surprising long-term stability of solutions prepared according to the present invention arises at least in part from the interaction between lactic acid (or the lactate molecule used in certain embodiments), the polar solvent (e.g., propylene glycol) and vancomycin.

In some aspects of the invention, the vancomycin is preferably present in the formulation as an HCl salt.

In some aspects of the invention, the vancomycin concentration calculated on the basis of the HCl salt in the inventive compositions is from about 25 mg/mL to about 150 mg/mL, preferably about 75 mg/mL to about 100 mg/mL. Some preferred concentrations of vancomycin include, for example, about 50 mg/mL or 100 mg/mL. In alternative aspects, the amount of vancomycin is outside these ranges but the amounts will be sufficient for single or multiple administrations of dosages generally regarded as effective amounts.

The compositions of the present invention can be maintained at a pH of from about 3 to about 8. Preferably, the composition is maintained at a pH of from about 4 to about 6. In at least one embodiment, the pH is about 5.5.

In some embodiments of the invention, an optional pH adjustor is included in the vancomycin-containing compositions. The pH adjustor may take the form of one or more basic compounds or conjugates of acids present in an amount sufficient to adjust or maintain the pH of the composition to the range set forth above, i.e. from about 3 to about 8, or to specific points in between such as about 4 or about 6. One preferred base is sodium hydroxide. Alternative bases are those commonly used in the art, including TRIS or other amine buffers, sodium hydroxide and calcium hydroxide. In some aspects the concentration of the base is about 1N or about 2N.

In some aspects of the invention, a lactate salt may be used in conjunction with or in place of lactic acid. In these embodiments, the optional pH adjustor may take the form of one or more acids or conjugate bases present in sufficient quantity to adjust the pH of the compositions to the ranges set forth above or to maintain the pH within these ranges, i.e. from about 3 to about 8, or to specific points in between such as about 4 or about 6. Alternative acids are those commonly used in the art, including but not limited to acetic acid, citric acid, hydrochloric acid, phosphoric acid and malic acid.

In some aspects of the invention, the concentration of lactic acid added either as the acid or as a salt is set to an appropriate level to obtain a stabilizing effect. For example, but not limited to, the compositions may comprise the addition of pre-made lactic acid solution, which may be from about 0.25M to about 1.5M. Preferably, the concentration of lactic acid solution used is from about 0.5M to about 1.25M or from about 0.75M to about 1M. More preferably, the concentration of the solution of lactic acid is about 1M.

Thus, the resulting final concentration of the lactic acid, lactate or mixtures thereof in the vancomycin-containing compositions of the present invention is preferably from about 0.25 mmole to about 0.94 mmole of lactic acid, lactate or mixtures thereof per mL of total vancomycin concentrate solution. This can be restated as about 22 to about 85 mg lactic acid per mL of total vancomycin concentrate solution. More preferably, the final concentration of the lactic acid or lactate in the vancomycin-containing compositions of the present invention is about 0.75 mmole per mL of total vancomycin concentrate, alternatively stated as 0.75M, or about 67 mg lactic acid per mL of total vancomycin concentrate solution.

In some aspects of the invention, the amount of lactic acid solution of 0.25M to 1.5M is added at about 50% (v/v) or about 75% (v/v). The lactic acid can be the DL form, the D form or the L form. Preferably, the DL form of lactic acid is used. Salts of lactic acid can also be added in conjunction with or in place of lactic acid at equivalent molar amounts that can easily be determined by one skilled in the art.

In several embodiments of the invention, the compositions include a polar solvent comprising propylene glycol, polyethylene glycol, or mixtures thereof. In some preferred aspects, the polar solvent is propylene glycol (PG) or polyethylene glycol (PEG) alone. For example, the compositions may include about 50% (v/v) of a lactic acid solution and about 50% (v/v) propylene glycol. Alternatively, the compositions may include about 75% (v/v) of a lactic acid solution and about 25% (v/v) propylene glycol. In another embodiment, the compositions may include about 50% (v/v) of a lactic acid solution and about 50% (v/v) polyethylene glycol. The amount of lactic acid solution and PG or PEG can also be varied within these ranges, i.e., the ratio of the lactic acid solution:PG or PEG in the compositions can range from about 50:50 to about 75:25. The molecular weight of the PEG will be within the range of pharmaceutically acceptable weights although PEG 400 is preferred in many aspects of the invention.

In some aspects of the invention, an antioxidant or free radical scavenging agent, e.g., methionine, is further included in the vancomycin-containing compositions. Other pharmaceutically-suitable antioxidants or free radical scavengers known in the art may be used, e.g., EDTA, citric acid, ascorbic acid, butylated hydroxytoluene (BHT), butylated hydroxy anisole (BHA), sodium sulfite, p-amino benzoic acid, glutathione, propyl gallate, cysteine, methionine and N-acetyl cysteine.

In view of the foregoing, some preferred vancomycin-containing compositions in accordance with the invention include:

I. a) vancomycin or a pharmaceutically acceptable salt thereof, in an amount of about 50 mg/mL or 100 mg/mL; and
  b) a pharmaceutically acceptable fluid having a pH of about 3 to about 8, comprising:
    i) about 25% (v/v) propylene glycol; and
    ii) about 0.75 mmole of lactic acid, lactate or mixtures thereof per mL of pharmaceutically acceptable fluid, produced for example by adding about 75% (v/v) of 1M lactic acid or lactate solution; and
    iii) sodium hydroxide in an amount sufficient to maintain the pH of said vancomycin-containing composition at about 5.5;

II. a) vancomycin or a pharmaceutically acceptable salt thereof, in an amount of about 50 mg/mL or 100 mg/mL; and
  b) a pharmaceutically acceptable fluid having a pH of about 3 to about 8, comprising:
    i) about 50% (v/v) propylene glycol; and
    ii) about 0.5 mmole of lactic acid, lactate or mixtures thereof per mL of pharmaceutically acceptable fluid, produced for example by adding about 50% (v/v) 1M lactic acid or lactate solution; and
    iii) sodium hydroxide in an amount sufficient to maintain the pH of said vancomycin-containing composition at about 5.5; and III. a) vancomycin or a pharmaceutically acceptable salt thereof, in an amount of about 50 mg/mL or 100 mg/mL; and
  b) a pharmaceutically acceptable fluid having a pH of about 3 to about 8, comprising:
    i) about 50% (v/v) polyethylene glycol;
    ii) about 0.5 mmole of lactic acid, lactate or mixtures thereof per mL of pharmaceutically acceptable fluid, produced for example by adding about 50% (v/v) of a 1M lactic acid or lactate solution; and
    iii) sodium hydroxide in an amount sufficient to maintain a pH of said vancomycin-containing composition at about 5.5.

Each of these compositions have the same stability profiles already described.

Another embodiment of the invention includes methods of treating a vancomycin-sensitive disease in mammals, i.e. a bacterial infection. The methods include administering, to a mammal in need thereof, an effective amount of a vancomycin-containing composition described herein. Since the active ingredient portion of the inventive compositions is an FDA-approved drug, those of ordinary skill will recognize that the doses of vancomycin employed in this aspect of the invention will be the similar to those employed in any treatment regimens designed for vancomycin as marketed. The patient package insert for vancomycin HCl containing dosing information is incorporated herein by reference. The methods of treatment also include administering the inventive formulations for any purpose or physical condition for which vancomycin has been found to be useful. In general, the daily intravenous dose may be typically from about 1 g to about 2 g, administered as about 250 mg to about 500 mg every 3 to 6 hours or as about 1 g every 12 hours.

Another embodiment of the invention includes methods of preparing vancomycin-containing compositions described herein. The methods include reconstituting lyophilized vancomycin to a concentration of about 25 mg/mL to about 150 mg/mL in a polar solvent comprising PG, PEG or mixtures thereof, lactic acid or a lactate salt, and an optional pH adjustor (i.e., an acid or base or combination thereof), in an amount sufficient to maintain the pH of the composition at from about 3 to about 8. The steps are carried out under pharmaceutically acceptable conditions for sterility and manufacturing.

The compositions of the present invention may be packaged in any suitable sterile vial, infusion bag or container fit for the sterile or non-sterile storage of a pharmaceutical such as vancomycin. Suitable containers can be of a size sufficient to hold one or more doses of vancomycin. Within this aspect from about 2 mL to about 200 mL of the inventive compositions are packaged as a single dose or a multi-dose. Preferably, from about 25 mL to about 100 mL, or from about 50 mL to about 100 mL are packaged in a container. More preferably, about 100 mL is packaged in a container. In some aspects of the invention, the concentration of the vancomycin-containing compositions in the containers is from about 25 mg/mL to about 150 mg/mL. Preferably, the concentration of the vancomycin-containing compositions is from about 50 mg/mL to about 100 mg/mL. In other aspects, the containers include from one to about 25 doses. Preferably, the containers include from about four to about 20 doses, or from about 10 to about 20 doses. In some aspects, the vancomycin-containing compositions of the present invention will be packaged in a vial. Typical Type 1 glass vials are considered appropriate for injection or infusion vials.

A further aspect of the invention includes a kit containing the vancomycin-containing compositions described herein. As will be appreciated by those of ordinary skill, the kit will contain at least one pharmaceutically acceptable vial or container containing one or more doses of the vancomycin-containing compositions as well as other pharmaceutically necessary materials for storing and/or administering the drug, including instructions for storage and use, infusion bag or container with normal saline (i.e., 0.9% sodium chloride) or 5% dextrose in water ($D_5W$), and/or additional diluents, if desired, etc.

In some embodiments, other excipients can also be added to adjust various properties of the formulation. For example, one or more antioxidants or free radical scavenging agents can be added to assist in improving the color changes that might occur. A preferred antioxidant is methionine, which can be added in a range of from about 0.25 mg to about 10 mg/mL, or more preferably in some embodiments at a concentration of about 4 mg to about 6 mg/mL.

In accordance with another aspect of the invention, there are provided vancomycin-containing compositions including:
  a) vancomycin or a pharmaceutically acceptable salt thereof, in an amount of about 2.5 mg/mL to about 10 mg/mL; and
  b) a pharmaceutically acceptable fluid having a pH of about 3 to about 8, comprising:
    i) about 1.20% (v/v) to about 5% (v/v) of a polar solvent comprising propylene glycol, polyethylene glycol, and mixtures thereof; and
    ii) about 0.04 mmole to about 1 mmole of lactic acid, lactate or mixtures thereof per mL of pharmaceutically acceptable fluid, produced for example, by using a 0.04M to 1M lactic acid, lactate solution or mixtures thereof (e.g., about 3 mg to about 90 mg lactic acid or lactate per milliliter of the vancomycin-containing composition); and
    iii) optionally, a pH adjustor, in an amount sufficient to maintain a pH of the vancomycin-containing composition at from about 3 to about 8.

These more dilute compositions are substantially free of precipitation after at least about 12 months of storage at a temperature of from about 5° C. to about 15° C. Preferably, the vancomycin-containing compositions are substantially free of precipitation for at least 24 months. The total impurities in the inventive compositions resulting from the degradation of vancomycin in the compositions is less than about 6% degradation of vancomycin B as determined by HPLC at a wavelength of 280 nm, after at least about 12 months of storage at a temperature of from about 5° C. to about 15° C. Preferably, the vancomycin-containing compositions are stable for at least about 24 months of storage at a temperature of from about 5° C. to about 15° C.

In some embodiments, the concentration of lactic acid, lactate or mixtures thereof, added to the compositions is from 0.05M to 0.15M (e.g., about 0.05 mmole to about 0.15 mmole per mL of the final vancomycin-containing composition). In another embodiment, the concentration of lactic acid or lactate is from 0.05M to 0.1M (e.g., about 0.05 mmole to about 0.1 mmole per mL of the final vancomycin-containing composition). The lactate can be selected from the DL form, the D form, the L form or mixtures thereof. Preferably, the DL form of lactic acid is used.

In other embodiments, the compositions include a polar solvent comprising propylene glycol, polyethylene glycol or mixtures thereof. Preferably, the polar solvent is propylene glycol (PG) or polyethylene glycol (PEG). For example, the compositions may include from about 1.25% (v/v) to about 2.5% (v/v) PG. Preferably, the compositions include 1.25% (v/v) or 2.5% PG (v/v). Alternatively, the compositions may include from about 1.25% (v/v) to about 2.5% (v/v) PEG. The molecular weight of the PEG will be within the range of pharmaceutically acceptable weights although PEG 400 is preferred in many aspects of the invention.

In some embodiments, the amount of vancomycin calculated on the basis of the HCl salt in the inventive compositions is generally at concentrations of from about 2.5 mg/mL to about 10 mg/mL. In another embodiment of the invention, the vancomycin concentration is from about 5 mg/mL to about 7.5 mg/mL. Preferably, the vancomycin concentration is about 5 mg/mL.

In some embodiments, the compositions include a pH modifier which is present in an amount sufficient to adjust the pH of the compositions to the ranges set forth above, i.e., from about 3 to about 8, or to specific points in between such as about 4 or about 6. Preferably, the pH of the vancomycin-containing compositions is about 4.5 or about 5.5. Either acids or bases, or mixtures thereof, may be used, depending on the need. If lactic acid is used as the source of lactate, one preferred base is sodium hydroxide. Alternative bases are those commonly used in the art, including TRIS or other amine buffers, and calcium hydroxide. Acids may also be used to titrate the pH to a point within the ranges described above, e.g., where a lactate salt is used.

In some embodiments, other excipients can also be added to adjust various properties of the formulation. For example, antioxidants or free radical scavenging agents may be added to assist in improving the color changes that might occur during storage.

In some aspects of the invention, the inventive compositions are maintained during storage and/or prior to use at a temperature of from about 5° C. to about 10° C. More preferably, the compositions are maintained at a temperature of about 5° C., i.e., under refrigerated conditions.

Preferred embodiments of the invention include vancomycin-containing compositions which include:
  I. A vancomycin-containing composition, comprising:
    a) vancomycin or a pharmaceutically acceptable salt thereof, in an amount of about 5 mg/mL; and
    b) a pharmaceutically acceptable fluid having a pH of about 3 to about 8, comprising:
      i) about 1.25% (v/v) propylene glycol;
      ii) about 0.05 mmole lactic acid, lactate or mixtures thereof per mL of vancomycin-containing composition (for example, about 4.5 mg lactic acid per mL of vancomycin-containing composition); and
      iii) optionally, a pH adjuster such as sodium hydroxide in an amount sufficient to maintain the pH of the vancomycin-containing composition at about 5.5.
  II. A vancomycin-containing composition, comprising:
    a) vancomycin or a pharmaceutically acceptable salt thereof, in an amount of about 5 mg/mL; and
    b) a pharmaceutically acceptable fluid having a pH of about 3 to about 8, comprising:

i) about 2.5% (v/v) propylene glycol;
ii) 0.1 mmole of lactic acid, lactate or mixtures thereof per milliliter of vancomycin-containing composition (for example, about 9 mg of lactic acid per ml of vancomycin-containing composition); and
iii) optionally, a pH adjuster such as sodium hydroxide in an amount sufficient to maintain a pH of the vancomycin-containing composition at about 5.5.

The stability profile of each of the above is the same as previously mentioned, i.e., they are substantially free of precipitation after at least about 12 months of storage at a temperature of about 5° C. to about 15° C.

Another embodiment of the invention includes methods of treating a vancomycin-sensitive disease in mammals, i.e. a bacterial infection. The methods include administering, to a mammal in need thereof, an effective amount of a vancomycin-containing composition described herein. Since the active ingredient portion of the inventive compositions is an FDA-approved drug, those of ordinary skill will recognize that the doses of vancomycin employed in this aspect of the invention will be the similar to those employed in any treatment regimens designed for vancomycin as marketed. The patient package insert containing dosing information is incorporated herein by reference. The methods of treatment also include administering the inventive formulations for any purpose or physical condition for which vancomycin has been indicated as being useful. The daily intravenous dose is from about 1 g to about 2 g, administered as about 250 mg to about 500 mg every 3 to 6 hours or as about 1 g every 12 hours.

Another embodiment of the invention includes methods of preparing vancomycin-containing compositions described herein. The methods include reconstituting lyophilized vancomycin to a concentration of about 2.5 mg/mL to about 10 mg/mL in a polar solvent comprising PG, PEG or mixtures thereof, lactate, lactic acid, or mixtures thereof, and an optional pH adjustor in an amount sufficient to maintain the pH of the composition at from about 3 to about 8. The steps are carried out under pharmaceutically acceptable conditions for sterility and/or bioburden and manufacturing.

The compositions of the present invention can be packaged in any suitable sterile vial, infusion bag or container fit for the appropriate storage of a pharmaceutical such as vancomycin. Suitable containers can be of a size sufficient to hold one or more doses of vancomycin. Within this aspect from about 25 mL to about 500 mL of the inventive compositions are packaged as a single dose or a multi-dose. Preferably, from about 25 mL to about 400 mL, or from about 50 mL to about 200 mL are packaged in a container. More preferably, about 100 mL is packaged in a container. In some aspects of the invention, the concentration of the vancomycin-containing compositions in the containers is from about 2.5 mg/mL to about 15 mg/mL, or from about 5 mg/mL to about 10 mg/mL. Preferably, the concentration of the vancomycin-containing compositions is about 5 mg/mL. In other aspects, the containers include from one to about 5 doses. Preferably, the containers include from about one to about four doses. In some aspects, the vancomycin-containing compositions of the present invention may be packaged in a vial. Typical Type 1 glass vials are a preferred vial.

EXAMPLES

The following examples serve to provide further appreciation of the invention but are not meant in any way to restrict the effective scope of the invention.

Examples 1-4

100 mg/mL Vancomycin

Example 1 (75% (v/v) 1M Lactic Acid Solution and 25% (v/v) PG)

A lactic acid solution was prepared by dissolving 7.68 g of an 88% lactic acid solution in 40 mL water for injection. The pH was then adjusted to 5.5 with a 2N sodium hydroxide solution. A 75:25 lactic acid:PG solution was prepared by adding 25 mL of PG to the above lactic acid solution, and the volume was made up to 100 mL with water for injection. 10 g of vancomycin HCl was then added to 75 ml of the 75:25 lactic acid:PG solution and the volume was made up to 100 mL with the 75:25 lactic acid:PG solution to yield a vancomycin concentration of 100 mg/mL. The sample was mixed well. 2N sodium hydroxide solution was added to the sample to bring the pH to 5.5.

Example 2 (50% (v/v) 1M Lactic Acid Solution and 50% (v/v) PG)

A lactic acid solution was prepared by dissolving 5.12 g of an 88% lactic acid solution in 40 mL water for injection. The pH was then adjusted to 5.5 with a 2N sodium hydroxide solution. A 50:50 lactic acid:PG solution was prepared by adding 50 mL of PG to the above lactic acid solution, and the volume was made up to 100 mL with water for injection. 10 g of vancomycin HCl was then added to 75 mL of the 50:50 lactic acid:PG solution and the volume was made up to 100 mL with the 50:50 lactic acid:PG solution to yield a vancomycin concentration of 100 mg/mL. The sample was mixed well. 2N sodium hydroxide solution was added to the sample to bring the pH to 5.5.

Example 3

Comparative (95% (v/v) 1M Lactic Acid Solution and 5% (v/v) PG)

A lactic acid solution was prepared by dissolving 9.728 g of an 88% lactic acid solution in 40 mL water for injection. The pH was then adjusted to 5.5 with a 2N sodium hydroxide solution. A 95:5 lactic acid:PG solution was prepared by adding 5 mL of PG to the above lactic acid solution, and the volume was made up to 100 mL with water for injection. 10 g of vancomycin HCl was then added to 75 mL of the 95:5 lactic acid:PG solution and the volume was made up to 100 mL with the 95:5 lactic acid:PG solution to yield a vancomycin concentration of 100 mg/mL. The sample was mixed well. 2N sodium hydroxide solution was added to the sample to bring the pH to 5.5.

Example 4

Comparative (87.5% (v/v) 1M Lactic Acid Solution and 12.5% (v/v) PG)

A lactic acid solution was prepared by dissolving 8.96 g of an 88% lactic acid solution in 40 mL water for injection. The pH was then adjusted to 5.5 with a 2N sodium hydroxide solution. A 87.5:12.5 lactic acid:PG solution was prepared by adding 12.5 mL of PG to the above lactic acid solution, and the volume was made up to 100 mL with water for injection. 10 g of vancomycin HCl was then added to 75 mL of the 87.5:12.5 lactic acid:PG solution and the volume was made up to 100 mL with the 87.5:12.5 lactic acid:PG solution to yield a vancomycin concentration of 100 mg/mL. The sample was mixed well. 2N sodium hydroxide solution was added to the sample to bring the pH to 5.5.

Control

A lactic acid solution was prepared by dissolving 10.24 g of an 88% lactic acid solution in 40 mL water for injection. The pH was then adjusted to 5.5 with a 2N sodium hydroxide solution. The volume was made up to 100 mL with water for injection. 10 g of vancomycin HCl was then added to the lactic acid solution to yield a vancomycin concentration of 100 mg/mL. The sample was mixed well. 2N sodium hydroxide solution was added to the sample to bring the pH to 5.5.

The samples were stored at 25° C. and were analyzed for visibly observable precipitation as reported in Table 1 below. The test data is reported in Table 1 below.

TABLE 1

Stability of Vancomycin Solutions (100 mg/mL) at pH 5.5

| Example | Formulation | Time to precipitation at 25° C. |
|---|---|---|
| Control | 1M Lactic acid | 6 days |
| 1 | 75:25 1M Lactic acid solution:PG | (no precipitation for at least ~1 year) |
| 2 | 50:50 1M Lactic acid solution:PG | (no precipitation for at least ~1 year) |
| 3 - Comparative | 95:5 1M Lactic acid solution:PG | 11 days |
| 4 - Comparative | 87.5:12.5 1M Lactic acid solution:PG | 16 days |

As shown in Table 1, the samples including the ratio of 1M lactic acid solution:PG within the range of from about 50:50 to about 75:25 demonstrate excellent stability, as the solutions were free of precipitation through at least one year at 25° C.

In contrast, the lactic acid solution control sample and the samples including a ratio of lactic acid:PG outside the amounts required herein, did not demonstrate physical stability. The samples exhibited precipitation within 16 days.

Example 5

100 mg/mL Vancomycin

A lactic acid solution was prepared by dissolving 7.68 g of an 88% lactic acid solution in 40 mL water for injection. The pH was then adjusted to 5.5 with a 2N sodium hydroxide solution. A 75:25 lactic acid:PG solution was prepared by adding 25 mL of PG to the above lactic acid solution, and the volume was made up to 100 mL with water for injection. 10 g of vancomycin HCl was then added to 75 mL of the 75:25 lactic acid:PG solution and the volume was made up to 100 mL with the 75:25 lactic acid:PG solution to yield a vancomycin concentration of 100 mg/mL. The sample was mixed well. 2N sodium hydroxide solution was added to the sample to bring the pH to 5.5.

The samples were stored at 25° C. and were tested after initial preparation, and again as indicated in Table 2 below.

The samples were tested to determine the amount of vancomycin B in the samples after storage. The test data is reported in Table 2 below.

TABLE 2

Stability of Vancomycin (100 mg/mL) in 75:25 1M Lactic acid:PG at pH 5.5 at 25° C.

| Batch # | Storage Period | % Vancomycin B | pH |
|---|---|---|---|
| VCM-49 | Initial | 93.3 | 5.4 |
| | 1 Month | 92.9 | 5.14 |
| | 2 Months | 92.5 | 5.05 |
| | 6 Months | 92.3 | 5.02 |
| | 12 Months | 91.9 | 5.10 |
| VCM-50 | Initial | 93.3 | 5.8 |
| | 1 Month | 92.9 | 5.21 |
| | 2 Months | 92.2 | 5.25 |
| | 8.5 Months | 91.9 | 5.15 |
| | 12 Months | 91.4 | 5.29 |
| VCM-51 | Initial | 93.5 | 5.56 |
| | 1 Month | 92.6 | 5.05 |
| | 2 Months | 92.3 | 5.03 |
| | 8 Months | 92.3 | 5.10 |

As shown in Table 2, vancomycin in 75:25 1M lactic acid solution:PG exhibited excellent stability at 25° C. The samples exhibited less than a 2% loss vancomycin B after more than 12 months of storage at 25° C. The data presented in Table 2 translates into vancomycin-containing compositions having a shelf life of at least 12 months at ambient or refrigerated conditions.

Example 6

50 mg/mL Vancomycin

A lactic acid solution was prepared by dissolving 3.84 g of an 88% lactic acid solution in 40 mL water for injection. The pH was then adjusted to 5.0 with a 2N sodium hydroxide solution. A 75:25 lactic acid solution:PG solution was prepared by adding 25 mL of PG to the above lactic acid solution, and the volume was made up to 100 mL with water for injection. 5 g of vancomycin HCl and 0.25 g of L-methionine were then added to 75 mL of the 75:25 lactic acid:PG solution and the volume was made up to 100 mL with the 75:25 lactic acid:PG solution to yield a vancomycin concentration of 50 mg/mL. The sample was mixed well. 2N sodium hydroxide solution was added to the sample to bring the final pH to 5.0. In previous studies, the vancomycin solutions turned pale yellow in color when exposed to long term storage conditions. This color change may be caused in part by the oxidative degradation of vancomycin or impurities present in the vancomycin drug substance. Therefore, methionine was included as an free radical scavenger and vials were filled under a nitrogen atmosphere. The head space oxygen in the following three batches ranged from 2% to 5%. Test data are reported in Table 3 below.

TABLE 3

Stability of Vancomycin (50 mg/mL) in 75:25 0.5M Lactic acid solution:PG at pH 5.0 to 4.5 at 25° C.

| Batch # | Storage Period (Months) | % Vancomycin B | pH |
|---|---|---|---|
| VCM-83 | Initial | 92.4 | 5.02 |
| | 1 | 92.0 | 4.98 |

TABLE 3-continued

Stability of Vancomycin (50 mg/mL) in 75:25 0.5M
Lactic acid solution:PG at pH 5.0 to 4.5 at 25° C.

| Batch # | Storage Period (Months) | % Vancomycin B | pH |
|---|---|---|---|
| | 3 | 91.0 | 4.95 |
| | 6 | 88.4 | 4.85 |
| | 12 | 87.3 | 4.82 |
| VCM-84 | Initial | 92.2 | 4.64 |
| | 1 | 91.9 | 4.76 |
| | 3 | 91.0 | 4.42 |
| | 6 | 86.9 | 4.58 |
| | 12 | 86.2 | 4.49 |
| VCM-87 | Initial | 91.7 | 4.40 |
| | 1 | 91.6 | 4.55 |
| | 3 | 89.3 | 4.88 |
| | 6 | 88.8 | 4.42 |

As shown on the table above, a 4 to 6% loss of vancomycin B-over a 12 month storage period at 25° C. was observed. Assuming an initial level of vancomycin B of 97-100%, one would expect a shelf life of 24 months at 25° C. storage assuming a minimum of 80% level of vancomycin B as recited in the USP monograph for vancomycin products.

Example 7

Vancomycin (100 mg/mL): ~8 L Batch Manufactured Under Aseptic Conditions

Vancomycin batches (VCM49-51) in Example 5 display excellent stability. A pilot scale batch was manufactured according to the Example 5 protocol and filled into vials to assess the chemical stability. The data are summarized in the Table 4 below

TABLE 4

Stability of Vancomycin (100 mg/mL) in 75% 1M lactic acid solution: 25% PG, methionine 5 mg/mL at pH 5.5

| Batch # | Temp. | Storage Time | % of VCM B | % of initial of VCM B | Area % of peak at RRT 0.66 | Area % of peak at RRT 1.81 | pH |
|---|---|---|---|---|---|---|---|
| VCM-118 | | Initial | 94.9 | 100 | 0.30 | 0.96 | 5.56 |
| | 30° C. | 3 M | 92.5 | 97.5 | 1.00 | 1.88 | 5.54 |
| | | 6 M | 90.4 | 95.3 | 1.27 | 2.43 | 5.52 |
| | 25° C. | 3 M | 93.0 | 98.0 | 0.67 | 1.25 | 5.54 |

As shown in the table above, vancomycin solutions prepared according to this protocol possess outstanding stability. Only about a 4% loss in vancomycin B was observed at 30° C. after six months. The increase in peak area % of two major degradation products was observed to be less than 1.5%.

Example 8

Vancomycin (5 mg/mL)

About 0.05M lactic acid solution was prepared by dissolving 0.772 g of an 88% lactic acid solution in 70 mL water for injection. A 1.25% (v/v) PG solution was prepared by adding 1.881 g of PG to the 0.05M lactic acid solution and mixed well. 1N sodium hydroxide was added to adjust the pH to 5.0. The volume was brought up to 150 mL with water for injection. 392.6 mg vancomycin was then added to 60 mL of the 0.05M lactic acid solution:PG mixture and mixed well. The volume of the solution was then made up to 75 mL with 0.05M lactic acid solution:PG mixture.

The same procedure was followed for preparing the above lactic acid solution with 1.25% (v/v) PG samples with pH 5.5 and 6.0. About 0.1M lactic acid solution was prepared by dissolving 1.549 g of an 88% lactic acid solution in 70 mL water for injection. A 1.25% (v/v) PG solution was prepared by adding 1.889 g of PG to the 0.1M lactic acid solution and mixed well. 1N sodium hydroxide was added to adjust the pH to 5.0. The volume was brought up to 150 mL with water for injection. 392.4 mg vancomycin was then added to 60 mL of the 0.1M lactic acid solution:PG mixture and mixed well. 1N sodium hydroxide was added to the solution, if necessary, to adjust the pH to 5.0. The volume of the solution was then made up to 75 mL with 0.1M lactic acid solution: PG mixture.

The same procedure was followed for preparing the above lactic acid solution with 1.25% (v/v) PG samples with pH 5.5 and 6.0. About 0.05M lactic acid solution was prepared by dissolving 0.775 g of an 88% lactic acid solution in 70 mL water for injection. A 2.5% (v/v) PG solution was prepared by adding 3.754 g of PG to the 0.05M lactic acid solution and mixed well. 1N sodium hydroxide was added to adjust the pH to 5.0. The volume was brought up to 150 mL with water for injection. 391.8 mg vancomycin was then added to 60 mL of the 0.05M lactic acid solution:PG mixture and mixed well. 1N sodium hydroxide was added to the solution, if necessary, to adjust the pH to 5.0. The volume of the solution was then made up to 75 mL with 0.05M lactic acid solution:PG mixture.

The same procedure was followed for preparing the above lactic acid solution with 2.5% (v/v) PG samples with pH 5.5 and 6.0. About 0.1M lactic acid solution was prepared by dissolving 1.554 g of an 88% lactic acid solution in 70 mL water for injection. A 2.5% (v/v) PG solution was prepared by adding 3.76 g of PG to the 0.1M lactic acid solution and mixed well. 1N sodium hydroxide was added to adjust the pH to 5.0. The volume was brought up to 150 mL with water for injection. 391.7 mg vancomycin was then added to 60 mL of the 0.1M lactic acid solution:PG mixture and mixed well. 1N sodium hydroxide was added to the solution, if necessary, to adjust the pH to 5.0. The volume of the solution was then made up to 75 mL with 0.1M lactic acid solution: PG mixture.

The same procedure was followed for preparing the above lactic acid solution with 2.5% (v/v) PG samples with pH 5.5 and 6.0. The samples were stored at 5° C. and were analyzed for visibly observable precipitation and were tested for impurities, after initial preparation and again after 6 months. The samples were also tested to determine the amount of vancomycin in the samples after storage. The test data is reported in Table 5 below.

TABLE 5

Stability of Vancomycin Solutions (5 mg/mL) in Lactic Acid and Propylene Glycol at 5° C. at pH about 5.0, 5.5 and 6.0

| Batch # | Lactic Acid (M) | % Propylene Glycol | Assay (Months) | % VCM-B | % of Initial | Area % RRT 0.66 | Area % RRT 1.81 | pH |
|---|---|---|---|---|---|---|---|---|
| VCM-55 pH-5.0 | 0.05 | 1.25 | Initial | 92.0 | 100.0 | 2.05 | 0.53 | 4.91 |
| | | | 6 | 91.1 | 99.0 | 2.02 | 1.29 | 4.79 |
| | | | 12 | 90.8 | 98.7 | 2.74 | 3.01 | 4.60 |
| VCM-56 pH-5.5 | 0.05 | 1.25 | Initial | 94.0 | 100 | 1.50 | 0.38 | 5.39 |
| | | | 6 | 92.6 | 98.5 | 2.08 | 1.31 | 5.04 |
| | | | 12 | 90.7 | 96.5 | 2.76 | 3.04 | 4.92 |
| VCM-57 pH-6.0 | 0.05 | 1.25 | Initial | 91.7 | 100 | 2.12 | 0.52 | 5.87 |
| | | | 6 | 90.5 | 98.7 | 2.09 | 1.39 | 5.29 |
| | | | 12 | 90.4 | 98.6 | 2.68 | 3.13 | 5.11 |
| VCM-58 pH-5.0 | 0.1 | 1.25 | Initial | 93.4 | 100.0 | 1.69 | 0.45 | 4.97 |
| | | | 6 | 92.5 | 99.0 | 1.88 | 0.95 | 4.77 |
| | | | 12 | 91.1 | 97.5 | 2.72 | 3.00 | 4.61 |
| VCM-59 pH-5.5 | 0.1 | 1.25 | Initial | 94.4 | 100.0 | 1.30 | 0.37 | 5.40 |
| | | | 6 | 93.6 | 99.2 | 1.91 | 0.96 | 4.89 |
| | | | 12 | 90.4 | 95.8 | 2.85 | 3.12 | 4.80 |
| VCM-60 pH-6.0 | 0.1 | 1.25 | Initial | 94.4 | 100.0 | 1.31 | 0.36 | 5.92 |
| | | | 6 | 93.1 | 98.6 | 1.91 | 1.00 | 5.29 |
| | | | 12 | 91.5 | 96.9 | 2.26 | 3.00 | 4.87 |
| VCM-61 pH-5.0 | 0.05 | 2.5 | Initial | 94.4 | 100.0 | 1.27 | 0.38 | 4.88 |
| | | | 6 | 92.8 | 98.3 | 2.05 | 1.23 | 4.5 |
| | | | 12 | 91.1 | 96.5 | 2.55 | 2.81 | 4.66 |
| VCM-62 pH-5.5 | 0.05 | 2.5 | Initial | 94.2 | 100 | 1.35 | 0.37 | 5.45 |
| | | | 6 | 92.8 | 98.5 | 2.08 | 1.30 | 5.04 |
| | | | 12 | 91.1 | 96.7 | 2.58 | 2.88 | 4.94 |
| VCM-63 pH-6.0 | 0.05 | 2.5 | Initial | 94.2 | 100.0 | 1.40 | 0.38 | 6.04 |
| | | | 6 | 92.6 | 98.3 | 2.19 | 1.43 | 5.26 |
| | | | 12 | 91.1 | 96.7 | 2.64 | 2.95 | 5.11 |
| VCM-64 pH-5.0 | 0.1 | 2.5 | Initial | 94.8 | 100.0 | 1.32 | 0.37 | 4.94 |
| | | | 6 | 93.5 | 98.6 | 1.92 | 0.97 | 4.70 |
| | | | 12 | 92.4 | 97.5 | 2.13 | 2.15 | 4.70 |
| VCM-65 pH-5.5 | 0.1 | 2.5 | Initial | 94.8 | 100.0 | 1.32 | 0.99 | 5.49 |
| | | | 6 | 93.5 | 98.6 | 1.93 | 1.02 | 5.01 |
| | | | 12 | 92.4 | 97.5 | 2.28 | 2.16 | 5.00 |
| VCM-66 pH-6.0 | 0.1 | 2.5 | Initial | 94.8 | 100.0 | 1.33 | 0.37 | 5.95 |
| | | | 6 | 93.4 | 98.5 | 2.01 | 1.09 | 5.14 |
| | | | 12 | 92.3 | 97.4 | 2.23 | 2.29 | 5.06 |

As can be seen in Table 5, the samples including the amount of PG from about 1.25% (v/v) to about 2.5% (v/v), as claimed, demonstrated excellent stability. The solutions were free of precipitation after 12 months at 5° C. The samples also exhibited less than 2 to 4% loss of vancomycin B after 12 months of storage at 5° C. The data presented in Table 5 suggests vancomycin-containing compositions according to the present invention have a shelf life of at least two years under refrigerated conditions.

I claim:

1. A vancomycin-containing composition, comprising:
a) about 25 mg/mL to about 150 mg/mL vancomycin or a pharmaceutically acceptable salt thereof; and
b) a pharmaceutically acceptable fluid having a pH of about 3 to about 8, comprising:
  i) about 25% (v/v) to about 50% (v/v) of a polar solvent comprising propylene glycol, polyethylene glycol or mixtures thereof; and
  ii) about 0.25 mmole to about 0.94 mmole of lactic acid, lactate or mixtures thereof per mL of pharmaceutically acceptable fluid;
wherein the vancomycin-containing composition has less than about 6% degradation of vancomycin B, as determined by HPLC at a wavelength of 280 nm, after at least about 12 months of storage at a temperature of from about 5° C. to about 25° C.; and
wherein the lactic acid, lactate or mixtures thereof and the polar solvent are present in the composition in amounts providing the composition with an equivalent of a 1M lactic acid to polar solvent ratio of 75:25 (v/v) to 50:50 (v/v) per 100 mg/mL of vancomycin.

2. The vancomycin-containing composition of claim 1, wherein the pH of said vancomycin-containing composition is from about 4 to about 6.

3. The vancomycin-containing composition of claim 1, further comprising a pH adjustor.

4. The vancomycin-containing composition of claim 3, wherein the pH adjustor is a base or conjugate of an acid.

5. The vancomycin-containing composition of claim 4, wherein the base comprises either an amine buffer, sodium hydroxide, calcium hydroxide, or mixtures thereof.

6. The vancomycin-containing composition of claim 4, wherein the base is sodium hydroxide.

7. The vancomycin-containing composition of claim 3, wherein the pH adjuster is an acid.

8. The vancomycin-containing composition of claim 7, wherein the acid comprises either acetic acid, citric acid, hydrochloric acid, phosphoric acid, malic acid, or mixtures thereof.

9. The vancomycin-containing composition of claim 1, wherein the pharmaceutically acceptable fluid comprises about 0.75 mmole of lactic acid, lactate or mixtures thereof per mL of pharmaceutically acceptable fluid.

10. The vancomycin-containing composition of claim 1, wherein the polar solvent is polyethylene glycol.

11. The vancomycin-containing composition of claim 10, wherein the pharmaceutically acceptable fluid comprises about 0.25 mmole to about 0.62 mmole of lactic acid, lactate or mixtures thereof per mL of pharmaceutically acceptable fluid and about 50% (v/v) polyethylene glycol.

12. A vancomycin-containing composition, comprising:
a) vancomycin or a pharmaceutically acceptable salt thereof, in an amount of about 100 mg/mL; and
b) a pharmaceutically acceptable fluid having a pH of about 3 to about 8, comprising:
i) about 50% (v/v) polyethylene glycol;
ii) about 0.5 mmole of lactic acid or lactate or mixtures thereof per mL of pharmaceutically acceptable fluid; and
iii) optionally, a pH adjuster in an amount sufficient to maintain the pH of the vancomycin-containing composition at about 5.5;
    wherein the vancomycin-containing composition has less than about 6% degradation of vancomycin B, as determined by HPLC at a wavelength of 280 nm, after at least about 12 months of storage at a temperature of from about 5° C. to about 25° C.; and
    wherein the lactic acid, lactate or mixtures thereof and the polar solvent are present in the composition in amounts providing the composition with an equivalent of a 1M lactic acid to polar solvent ratio of 75:25 (v/v) to 50:50 (v/v).

13. A vancomycin-containing composition, comprising:
a) vancomycin or a pharmaceutically acceptable salt thereof, in an amount of about 50 mg/mL; and
b) a pharmaceutically acceptable fluid having a pH of about 3 to about 8, comprising:
i) about 50%) (v/v) polyethylene glycol;
ii) about 0.5 mmole of lactic acid, lactate or mixtures thereof per mL of pharmaceutically acceptable fluid; and
iii) optionally, a pH adjuster in an amount sufficient to maintain the pH of the vancomycin-containing composition at about 5.5;
    wherein the vancomycin-containing composition has less than about 6% degradation of vancomycin B, as determined by HPLC at a wavelength of 280 nm, after at least about 12 months of storage at a temperature of from about 5° C. to about 25° C.; and
    wherein the lactic acid, lactate or mixtures thereof and the polar solvent are present in the composition in amounts providing the composition with an equivalent of a 0.5 M lactic acid to polar solvent ratio of 75:25 (v/v) to 50:50 (v/v).

14. A vancomycin-containing composition, comprising:
a) vancomycin or a pharmaceutically acceptable salt thereof, in an amount of about 2.5 mg/mL to about 10 mg/mL; and
b) a pharmaceutically acceptable fluid having a pH of about 3 to about 8, comprising: i) about 1.25% (v/v) to about 5% (v/v) of a polar solvent comprising propylene glycol, polyethylene glycol, or mixtures thereof;
ii) about 0.04 mmole to about 1 mmole of lactic acid, lactate or mixtures thereof per mL of pharmaceutically acceptable fluid; and
iii) optionally, a pH adjuster in an amount sufficient to maintain the pH of the vancomycin-containing composition at from about 3 to about 8;
    wherein the vancomycin-containing composition has less than about 6% degradation of vancomycin B, as determined by HPLC at a wavelength of 280 nm, after at least about 12 months of storage at a temperature of from about 5° C. to about 15° C.; and
    wherein the lactic acid, lactate or mixtures thereof and the polar solvent are present in the composition in amounts providing the composition with an equivalent of a 1M lactic acid to polar solvent ratio of 75:25 (v/v) to 50:50 (v/v) per 100 mg/mL of vancomycin.

15. The vancomycin-containing composition of claim 14, wherein the polar solvent is polyethylene glycol.

16. The vancomycin-containing composition of claim 15, wherein the amount of polyethylene glycol is from about 1.25% (v/v) to about 2.5% (v/v).

17. The vancomycin-containing composition of claim 14, wherein the vancomycin-containing composition is substantially free of precipitation after at least about 12 months of storage at a temperature of from about 5° C. to about 15° C.

18. The vancomycin-containing composition of claim 14, wherein the amount of vancomycin is from about 5 mg/mL to about 7.5 mg/mL.

19. The vancomycin-containing composition of claim 14, wherein the amount of vancomycin is about 5 mg/mL.

\* \* \* \* \*